United States Patent [19]

Baggiolini et al.

[11] Patent Number: 5,039,671
[45] Date of Patent: Aug. 13, 1991

[54] NOVEL TRIFLUORINATED-1α,25S-DIHYDROXY VITAMIN D3 COMPOUNDS

[75] Inventors: Enrico G. Baggiolini, North Caldwell; Giacomo Pizzolato, Glen Ridge; Gary A. Truitt, Bloomfield; Milan R. Uskokovic, Upper Montclair, all of N.J.

[73] Assignee: Hoffmann-La Roche Inc., Nutley, N.J.

[21] Appl. No.: 438,547

[22] Filed: Nov. 16, 1989

Related U.S. Application Data

[60] Division of Ser. No. 821,299, Jan. 22, 1986, Pat. No. 4,906,785, which is a continuation-in-part of Ser. No. 683,442, Dec. 19, 1984, abandoned.

[51] Int. Cl.$^5$ .................... A01N 45/00; C07J 172/00
[52] U.S. Cl. .................................. 514/167; 552/653
[58] Field of Search ...................... 552/653; 514/167

[56] References Cited

U.S. PATENT DOCUMENTS

| | | | |
|---|---|---|---|
| 4,229,358 | 10/1980 | DeLuca et al. | 260/397.2 |
| 4,391,802 | 7/1983 | Suda et al. | 424/236 |
| 4,906,785 | 3/1990 | Baggiolini et al. | 568/33 |

OTHER PUBLICATIONS

Proceedings of the Fifth Workshop on Vitamin D 1982, p. 1079–1084.
Koeffler et al. Cancer Research, 44,5624–5628, Dec. 1984.
Dokah, S. et al., Endocrinology 112:200–206, 1983.
Murao, S. Cancer Research 43(8):4989–4996, 1983.
Reitsma P. et al., J. Cell. Biol. 97(5):347a, 1983.
Rigby, W. F. C. et al., Blood 62(5):153a, 1983.
Olsson, I. and Lund, U., Cancer Research 43 5862–5867, 1983 Eisman, J. A. et al., Lancet, Dec. 22/29:1335–1336, 1979.
Frampton, R. J. et al., Cancer Research 42:1116–1119, 1982.
Colston, K. et al., Cancer Research 42:856–859, 1982.
Sher, E. et al., Biochem. 200: 315–320, 1981.
Frampton, R. J. et al., Cancer Research 43:4443–4447, 1983.
Shiina, Y. et al., Arch Biochem. Biophys 220:90–94, 1983.
Abe, E. et al., Proc. Natl. Acad. Sci. U.S.A. 78:4990–4994, 1981.
McCarthy, D., Exp. Hematol 11 (Suppl. 14):200, 1983.
Honma Y. et al., Proc. Natl., Acad. Sci. U.S.A. 80:201–204, 1983.
Sato, T. et al., Tohoku J. Exp. Med. 138:445–446, 1982.
McCarthy, D. M. et al., Lancet Jan. 14:78–80, 1984.
Kobayashi et al., Tetrahedron, vol. 22, No. 43, pp. 4309–4312, (1981).

Primary Examiner—Frederick E. Waddell
Assistant Examiner—T. J. Criares
Attorney, Agent, or Firm—George M. Gould; Bernard S. Leon; Ellen Ciambrone Coletti

[57] ABSTRACT

26, 26, 26-Trifluoro-1α, 25-dihydroxy-cholecalciferol, and the 25R or 25S epimer thereof, are described, as well as processes and intermediates utilized to prepare the same, as well as pharmaceutical compositions containing the same. 26,26,26-trifluoro 1α, 25-dihydroxy-cholecalciferol and the 25R or 25S epimer thereof are useful agents in the treatment of disease states such as osteoporosis, oseodystrophy and leukemia.

3 Claims, No Drawings

TRIFLUORINATED-1α,25S-DIHYDROXY VITAMIN D3 COMPOUNDS

This is a division of application Ser. No. 06/821,299, filed Jan. 22, 1986, now U.S. Pat. No. 4,906,785 which is a continuation-in-part of application Ser. No. 06/683,442, filed Dec. 19, 1984 abandoned.

BACKGROUND OF THE INVENTION

It has been known in the art to introduce fluorines on the 26 and 27 carbon atom in certain vitamin $D_3$ metabolites in order to enhance vitamin D like activity. Thus, for example, U.S. Pat. No. 4,358,406 describes 26,26,26,27,27,27-hexafluoro-1α,25-dihydroxycholecalciferols which are indicated to have greater vitamin D-like activity compared to the analogous unfluorinated compounds. The compounds of the patent are indicated to be useful in human and veterinary medicine for treatment of calcium and phosphorus deficiency or imbalance. These compounds are thus useful in the treatment of hypoparathyroidism, pseudohypoparathyroidism, renal osteodystrophy, osteoporosis and other bone disorders symptomatic of calcium and phosphorus imbalance. Veterinary applications include, for example, treatment of milk fever in cattle, leg weakness in turkeys, chickens and other domestic animals. Indicated therapeutic dosages for the above indications ranged from 0.1 to micrograms/day orally or parenterally.

In U.S. Pat. No. 4,298,791 there is disclosed 25-hydroxy-26,26,26,27,27,27-hexafluorocholecalciferol. This compound is indicated to have excellent vitamin $D_3$-like activity as measured by ability to stimulate calcium transport in the intestine and to mobilize calcium from bone and in its antirachitic activity. Thus the compound is useful in treatment of disease resulting from calcium metabolism disorder.

Kobayashi et al., Tetrahedron Letters, 22 (No 43), 4309 (1981) describe the synthesis of 26,26,26-trifluoro-25-hydroxyvitamin $D_3$ and 27-nor-26,26,26-trifluoro-25-hydroxyvitamin $D_3$. No biological activity was reported although the purpose of synthesis was to compare boneresolving activity with the previously described hexafluoro analogs of vitamin $D_3$.

SUMMARY OF THE INVENTION

The present invention relates to novel trifluorocholecalciferol derivatives that exhibit enhanced vitamin $D_3$-like activity. More particularly the present invention relates to 26,26,26, trifluoro-1α,25-dihydroxycholecalciferol, particularly in its 25-epimeric forms, which are unexpectedly more potent than other vitamin $D_3$ derivatives and analogs in assays which predict vitamin $D_3$-like, anti-proliferative and cellular differentiation inducing activities. Further aspects of the invention relate to the processes and novel intermediates utilized to prepare the desired end products and pharmaceutical preparations containing the biologically active end products.

DESCRIPTION OF THE INVENTION

The novel trifluoro compounds of the present invention are conveniently prepared by synthesis from the novel indene sulfone intermediate of the structure:

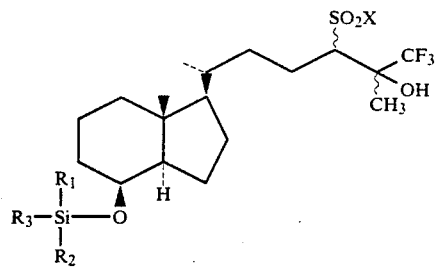

where X is aryl, preferably phenyl and $R_1$, $R_2$, $R_3$ each independently is lower alkyl, aryl or aralkyl, preferably $R_3$ is, (1,1-dimethylethyl) and $R_1$ and $R_2$ each are methyl.

In such synthesis the compounds of formula I above as an epimeric mixture of arylsulfonyls at the 4 position are dearylsulfonylated with an alkali metal or with an alkali metal amalgam and in the presence of an alkali metal phosphate. This reaction is conveniently carried out in a suitable inert organic solvent or solvent mixture such as a lower alkanol or cyclic ether or preferably mixtures thereof. A preferred reactant is sodium amalgam and dipotassium hydrogen phosphate, while preferred solvents include methanol, tetrahydrofuran and a mixture of methanol and tetrahydrofuran most preferably a 1:1 (v/v) mixture.

The alkali metal amalgam addition is carried out with cooling, preferably at temperatures below 0° C., most preferably at about −20° C.

Purification of the reaction products is carried out using chromatographic procedures known per se. Thus, in preferred embodiments silica column chromatography, provides the reaction product of formula II below in purified form:

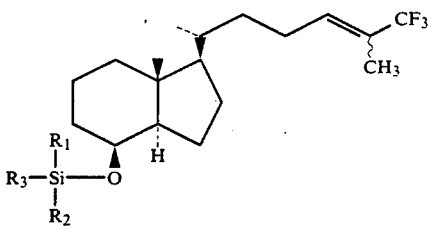

where $R_1$, $R_2$ and $R_3$ are as above

In the next step of the synthesis, the protected compounds of formula II are reacted with an epoxidation agent such as a peracid, most preferably trifluoro-peracetic acid at reduced temperatures such as at 0° C. Preferably the reaction is carried out in the presence of an inorganic base, such as for example a phosphate base most preferably dipotassium hydrogen phosphate. Suitable inert organic solvents may be employed for the reaction. Preferred for this purpose are halogenated alkyl or aryl solvents, most preferably chlorinated alkylenes such as methylene chloride. Under the conditions of the reaction part of the resulting product may consist of the desilylated product. Thus the product of the reaction is a mixture of the structures indicated below:

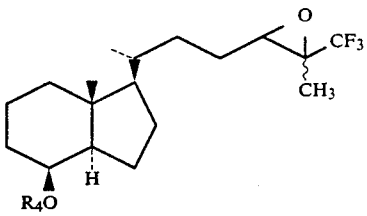

where R₄ is

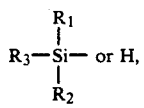

where R₁, R₂ and R₃ are as above.

Both the protected and unprotected compounds of formula III can be used in the succeeding step. Thus, after purification from the above reaction mixture using methods known per se, such as flash chromatography either or both of a mixture of the two components of formula III can be treated with a chemical reducing agent, such as an alkali metal or metal-hydride preferably lithium aluminum hydride in an inert organic solvent, most preferably an alkyl ether such as ethyl ether. The reaction is preferably carried out under ambient conditions of temperature and pressure, most preferably under an inert atmosphere such as an argon atmosphere. There is thus produced the corresponding protected and/or unprotected compounds of the formula:

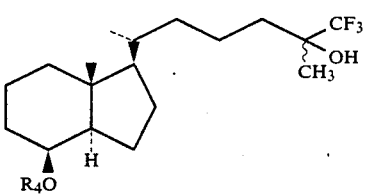

where R₄ is as above.

The compounds of formula IV can be conveniently purified using chromatographic procedures known per se, such as silica gel chromatography. It should be noted that the compounds of formula IV represent a mixture of epimers at the 5-position in the side chain.

The compounds of formula IV are then treated with a cation exchange resin to deprotect any silylated compound. The mixture of epimers can be separated, after purification by silica chromatography, by using high performance liquid chromatogarphy on a silica column. The selection of a silica column is not critical. A suitable silica column for this purpose is sold under the trademark Magnum 9 Partisil-10 by Whatman Inc. of Clifton, N.J. although any conventional HPLC silica column may be employed. To produce end products which are mixtures of epimers, the high performance liquid chromatography step can be eliminated.

The compounds of formula IV where R₄ is hydrogen are then oxidized using an oxidative agent. Suitable oxidative agents useful in oxidation of the 4-ring hydroxyl group include chromate salts, particularly with basic organic amines, such as, for example, pyridinium halochromates, preferably pyridinium chlorochromate. The reaction is carried out under ambient conditions of temperature and pressure using an inert solvent. Suitable inert solvents include the halogenated alkanes, preferably a chloroalkene such as methylene chloride. There is thus obtained ketones of the formula

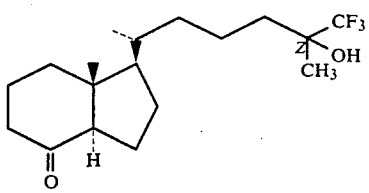

wherein Z is R-, S- or an R-, S- mixture

The ketones of formula V are then converted to their side chain hydroxy protected forms without isolation. Thus ketones of formula V are treated with a trialkylsilylization agent, preferably a trimethylsilylization agent to introduce a trimethylsilyl protecting group on the side chain hydroxy. A most preferred reagent for this purpose is trimethylsilylimidazole. The reaction is conveniently carried out at ambient temperature, preferably under an inert atmosphere.

The resulting protected compounds of the formula:

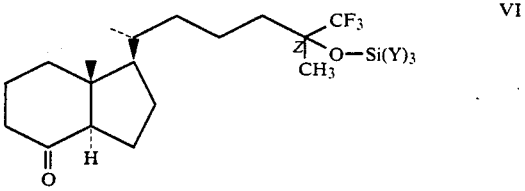

wherein Y is alkyl and Z is R-, S- or an R-, S-mixture are reacted with the carbanion of [3S-(3α,5β,Z)]-2-[2-methylene-3,5-bis[(1,1-dimethylethyl)dimethylsilyl]oxy]cyclohexylidene]ethyldiphenyl phosphine oxide followed by removal of the trialkylsilyl protecting groups to yield the desired end products of the invention, particularly: (A) 26,26,26,-trifluoro-1α,25S-dihydroxy cholecalciferol (B) 26,26,26-trifluoro-1α,25R-dihydroxy cholecalciferol.

The above reaction is carried out at reduced temperatures e.g. below −50° C., most preferably at about −78° C. using an inert atmosphere such as for example an argon atmosphere. A suitable inert solvent may be employed in carrying of this reaction, for example, a cyclic ether, most preferably tetrahydrofuran. The conversion of the phosphine oxide to the corresponding carbanion is readily accomplished by treating the phosphine oxide with an alkyl lithium such as preferably n-butyl lithium.

Removal of the trialkylsilyl protecting group can readily be accomplished by treating the reaction product with a cation exchange resin under ambient conditions in a suitable solvent such as a halogenated alkane, or preferably methylene chloride.

The final products of the invention can be purified by procedures known per se such as, for example, by use of silica gel chromatography.

The novel starting materials of formula I used in the above described synthesis are readily obtainable from known compounds available in the art. Thus, for example, [1R-[1β,[αS*,βS*],3aα,4aβ,7aβ]]-octahydro-β,7a-dimethyl-4-[[(1,1-dimethylethyl)dimethylsilyl]oxy]-α-ethenyl-1H-indene-1-ethanol can be converted into [1R-[1β(R*),3aα,4β,7aβ]]-1-(4-chloro-1-methyl-2-butenyl)- octahydro-4-[[(1,1-dimethylethyl)dimethylsilyl]oxy]-7a-methyl-1H-indene by treatment with thionyl chloride in the presence of pyridine. The resulting allylic chloride is then reacted with an aryl sulfinic acid salt, preferably benzene sulfinic acid sodium salt to yield the corresponding arylsulfonyl compound, e.g., [1R-[1β(R*),3aα,4β,7aβ]-1-[4-phenylsulfonyl)-1-methyl-2-butenyl)octahydro-4-[[(1,1-dimethylethyl)dimethylsilyl]oxy]-7a-methyl-1H-indene. The aforesaid indene is then catalytically hydrogenated using a palladium-on-carbon catalyst to provide the corresponding side chain saturated compound [1R-[1β(R*),3aα,4β,7aβ]]-1-[4-(phenylsulfonyl)-1-methylbutyl)-octahydro-4-[[1,1-dimethylethyl)dimethylsilyl]oxy]-7a-methyl-1H-indene. The completion of the side-chain to produce a compound of formula I is accomplished by reacting the carbanion of the aforesaid sulfonyl compound, formed by treatment with n-butyl lithium or lithium diisopropylamide, with trifluoroacetone.

The specific details of each of the reaction steps used in producing the intermediates of formula I according to the synthetic steps outlined above are set forth in the accompanying Examples below.

The compounds of the present invention can be administered in dosages that are in the range of about 0.10–3.0 micrograms/per day for the treatment of such disease states as osteoporosis, osteodystrophy, steroid induced osteopenia, hypoparathyroidism, hypophosphatemic rickets and hypophosphatemic osteomalacia which are characterized by lower than normal levels of endogeneously produced 1α,25-dihydroxycholecalciferol. The compounds of the invention are also powerful specific inducers of cell differentiation and inhibitors of cell proliferation. Thus, such compounds are useful agents in the treatment of proliferative disease states such as leukemia. Preferable dosage ranges are 0.25–2.0 micrograms per day for the treatment of the aforementioned disease states. The compounds of the invention can be administered orally, subcutaneously, intramuscularly, intravenously, intraperitoneally or topically.

The aforesaid products of the invention can be formulated into compositions such as tablets, capsules, and the like, or elixers for oral administration, or in sterile solutions or suspensions for parenteral administration for the treatment of the aforementioned disease states. About 0.10–3.0 micrograms, preferably 0.25–2.0 micrograms, is compounded with a pharmaceutically acceptable vehicle, carrier, excipient, binder, preservative, stablizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as calcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

The above products of the invention can be administered for the treatment of milk fever in pregnant ruminant animals prior to parturation in dosages in the range of 25–200 micrograms/day using conventional formulations.

Sterile compositions for injection and/or topical administration can be formulated according to conventional practice by dissolving or suspending the respective products of the invention in a vehicle such as a 10–20% ethanol-water mixture, a 10–20% propylene glycol-water mixture a naturally-occurring vegetable oil, such as sesame oil, peanut oil, cottonseed oil, and the like, or a synthetic fatty vehicle such as ethyl oleate or the like. For example, a suitable formulation for intravenous injection would be 2–3 ml of a 10–20% ethanol-water solution or a 10–20% propylene glycol-water mixture containing 25–200 micrograms of the products of the invention. Such a formulation would preferably contain 200–1000 micrograms of the products of the invention. Exemplary of a suitable formulation for topical administration would be a vegetable oil solution or suspension containing 25–200 micrograms of the products of the invention. Such a formulation would preferably contain 200–1000 micrograms of a product of the invention.

The aforesaid products of the invention can also be formulated for oral administration by incorporation of 25–200 micrograms of such product into fatty acid pellets.

The subject products may also be formulated for intramuscular injection by suspension of 100–1500 micrograms of such product in a vehicle such as a vegetable oil, an ethanol-water solution containing from 80–95% ethanol or a propylene glycol-water solution containing from 80–95% propylene glycol.

Buffers, preservatives, antioxidants and the like can be incorporated into the foregoing formulations as required.

As used throughout the specification and the appended claims, the term "lower alkyl" refers to a monovalent substituent consisting solely of carbon and hydrogen of from 1 to 8 carbon atoms which may be straight or branched-chain. Examples of lower alkyl groups are methyl, ethyl, n-propyl, i-propyl, tert.-butyl, hexyl, heptyl, octyl and so forth. The term "lower alkylene group" refers to a divalent substituent consisting solely of carbon and hydrogen of from 1 to 8 carbon atoms which may be straight or branched-chain and whose free valences are attached to two distinct groups. Examples of alkylene groups are methylene, ethylene, propylene and so forth. The term "lower alkoxy" refers to a lower alkyl group attached to the remainder of the molecule by oxygen. The term "aralkyl" refers to aryl lower alkyl groups such as benzyl, phenethyl and the like.

Examples of alkoxy groups are methoxy, ethoxy, isopropoxy, tert.-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term "aryl" means phenyl and substituted phenyl. The term "substituted" as applied to "phenyl" refers to phenyl which is substituted with one or more of the following groups: alkyl, halogen (i.e., fluorine, chlorine, bromine or iodine), nitro, cyano, trifluoromethyl and so forth. The term "alkanol" refers to a compound derived by protonation of the oxygen atom of an alkoxy group. Examples of alkanols are methanol, ethanol, 2-propanol, 2-methyl-2-propanol and the like. The term "alkali metal" refers to lithium, sodium and potassium.

In the formulas presented herein, the various substituents are illustrated as jointed to the steroid nucleus by one of these notations: a solid line (—) indicating a substituent which is in the β-orientation (i.e., above the plane of the molecule), a dotted line (---) indicating a substituent which is in the α-orientation (i.e., below the plane of the molecule), or a wavy line (∼∼∼)indicating a substitutent which may be in the α- or β-orientation. The formulae have all been drawn to show the compounds in their absolute stereochemical configurations. Since the starting materials are derived from a naturally occurring steroid, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively.

The nomenclature adopted to define absolute configuration of substituents bound to carbon atom 24 of the steroid nucleus is described in the Journal of Organic Chemistry, 34, 2849 (1970) under the title "IUPAC Tentative Rules for the Nomenclature of Organic Chemistry. Section E. Fundamental Stereochemistry."

EXAMPLE 1

Preparation of
[1R-[1β(R*),3aα,4β,7aβ]]-1-(4-chloro-1-methyl-2-butenyl)-octahvdro-4-[[(1,1-dimethylethyl)dimethylsilyl]oxy]-7a-methyl-1H-indene A solution of 2.9 g (8.22 mmol) of [1R-[1β,[αS*,βS*]],3aα,4aβ,7aβ]]-octahydro-β,7a-dimethyl-4-[[(1,1-dimethylethyl)dimethylsilyl]oxy]-α-ethenyl-1H-indene-1-ethanol in 100 mL of anhydrous ether was cooled at 0° C. and treated dropwise and under argon with 2.76 mL (37.84 mmol) of thionyl chloride, followed by 0.276 mL of pyridine. The mixture was allowed to stir at 0° C. for 2 h, then it was quenched by addition of 50 mL nf a 2N sodium potassium tartrate solution. The ether phase was separated and the aqueous phase extracted with ethyl acetate. The combined organic phases were washed with 1N hydrochloric acid, water, 2N potassium bicarbonate solution and brine, dried (Na₂SO₄) and evaporated. The solvent evaporated in vacuo and the residue purified by rapid chromatography on silica (eluent: hexane-ethyl acetate, 19:1(v:v)) to give 2.9 g (95% yield) of the title compound, as a low melting solid.

EXAMPLE 2

Preparation of
[1R-[1β(R*),3aα,4β,7aβ]]-1-[4-(phenylsulfonyl)-1-methyl-2-butenyl)-octahydro-4-[[(1,1-dimethylethyl)-dimethylsilyl]oxy]-7a-methyl-1H-indene A solution of 2.9 g (7.81 mmol) of [1R-[1β(R*),3aα,4β,7aβ]]-1-(4-chloro-1-methyl-2-butenyl)-octahydro-4-[[(1,1-dimethylethyl)dimethylsilyl]oxy]-7a-methyl-1H-indene in 130 mL of hexamethylphosphboramide was treated with 10.1 g (61.52 mmol) of benzene sulfinic acid sodium salt and stirred at room temperature under argon for 24 h. Ice water was then added (130 mL) and, after stirring for 30 min, the mixture was extracted with ethyl acetate. The combined extracts were washed with water (6x) dried (Na,SO₄), evaporated to dryness and the residue purified by rapid chromatography through silica, eluting with hexane-ethyl acetate (39:1 (v:v)) to give 3.5 g (94% yield) of the above-captioned product as a low melting solid.

EXAMPLE 3

Preparation of
[1R-[1β(R*),3aα,4β,7aβ]]-1-[4-(phenylsulfonyl)-1-methylbutyl)-octahydro-4-[[(1,1-dimethylethyl)dimethylsilyl]oxy]-7a-methyl-1H-indene A solution of 1.00 g (2.10 mmol) of [1R-[1β(R*),3aα,4β,7aβ]]-1-[4-(phenylsulfonyl)-1-methyl-2-butenyl)octahydro-4-[[(1,1-dimethylethyl)-dimethylsilyl]-oxy]-7a-methyl-1H-indene in 40 mL of ethanol was hydrogenated at room temperature and under normal pressure over 350 mg of 10% palladium-on-carbon. After 2 h, the catalyst was filtered and the filtrate evaporated to dryness to give 1.00 g of the above captioned product.

EXAMPLE 4

Preparation of
[1R-[1β(1R*),3aα,4β,7aβ]]-Octahydro-1-6,6,6-trifluoro-5-hydroxy-1,5-dimethyl-4-(phenylsulfonyl)hexyl]-4-[[(1,1-dimethylethyl)dimethylsilyl]-oxy]-7a-methyl-1H-indene A solution of 0.440 mL (3.14 mmol) of diisopropylamine in 10 mL of anhydrous tetrahydrofuran was cooled at 0° C. and treated dropwise under argon with 1.87 mL (2.99 mmol) of a 1.6 molar solution of n-butyllithium in hexane. After stirring for 15 min at 0° C., the resulting solution was cooled at −78° C. and diluted with 10 mL of anhydrous tetrahydrofuran. It was then treated dropwise with a solution of 1.00 g (2.09 mmol) of [1R-[1β(R*),3aα,4β,7aβ]]-1-[4-(phenylsulfonyl)-1-methylbutyl)-octahydro-4-[[(1,1-dimethylethyl)dimethylsilyl]oxy]-7a-methyl-1H-inolene in 15 mL of tetrahydrofuran and stirred at −78° C. for 5 min, then at 0° C. for 30 min. After cooling again at −78° C., the mixture was treated with 0.50 mL (5.59 mmol) of 1,1,1-trifluoroacetone and stirred at the same temperature for 1.5 h. It was then quenched by addition of 30 mL of a 1:1 mixture of 2N sodium potassium tartrate and 2N potassium bicarbonate solution, allowed to come at room temperature and extracted with methylene chloride. The combined organic extracts were washed with brine, dried (Na₂SO₄) and evaporated to dryness. The residue was purified by flash chromatography through silica (eluent hexane-ethyl acetate, 39:1 (v:v)) to give 0.71 g of the above captioned product as a colorless oil.

EXAMPLE 5

Preparation of
[1R-[1β(R*),3aα,4β,7aβ]]-Octahydro-1-[6,6,6-trifluoro-1,5-dimethyl-4-hexenyl]-4-[[(1,1-dimethylethyl)dimethylsilyl]oxy]-7a-methyl-1H-indene A solution of 0.56 g (0.95 mmol) of the sulfone product of Example 4 (epimeric mixture) in 18 mL of tetrahydrofuran and 18 mL of methanol was treated with 10 g of dipotassium hydrogen phosphate and after cooling at −20° C., with 11 g of 6% sodium amalgam. After stirring the resulting mixture at −20° C. for 10 min, 30 mL of brine was added, allowed to come to room temperature and extracted with ethyl acetate. The combined organic extracts were washed with brine, dried (Na$_2$SO$_4$,) and evaporated to dryness. The residue was purified by chromatography through silica (eluting with hexane-ethyl acetate, 39:1 (v:v)) to give 0.40 g of the above-captioned olefin as a colorless oil (mixture of geometrical isomers).

EXAMPLE 6

Preparation of
[1R-[1β(1R*),3aα,4β,7aβ]]-Octahydro-1-[6,6,6-trifluoro-1,5-dimethyl-24,25-epoxyhexyl]-4-[[(1,1-dimethylethyl)dimethylsilyl]oxy]-7a-methyl-1H-indene.

A solution of 0.260 mL (1.84 mmol) of trifluoroperacetic anhydride in 5 mL of anhydrous methylene chloride was cooled at 0° C., treated with 0.052 mL (1.89 mmol) of 90% hydrogen peroxide and stirred for 30 min. The resulting solution was rapidly added to 400 mg of the product of Example 5 (0.92 mmol) and 1.5 g of dipotassium hydrogen phosphate in 5 mL of methylene chloride at 0° C. After addition, the mixture was allowed to come to room temperature for 30 min, quenched with 5 mL of a 10% aqueous solution of sodium sulfite, diluted with 10% aqueous sodium bicarbonate solution and extracted with methylene chloride. The combined organic extracts were washed with brine, dried and evaporated to give 190 mg of pure protected product (mixture of epimers) and 140 mg of desilylated product. After flash chromatography purification, both products can be used in the next step.

EXAMPLE 7

Preparation of
[1R-[1β(1R*)-3aα,4β,7aβ]]Octahydro-1-[6,6,6-trifluoro-5-hydroxy-1,5-dimethylhexyl]-4-[[(1,1-dimethylethyl)dimethylsilyl]oxy]-7a-methyl-1H-indene To a suspension of 100 mg (2.63 mmol) of lithium aluminum hydride in 3 mL of anhydrous ether, a solution of 190 mg (0.42 mmol) of the protected product of Example 6 in 2 mL of ether was rapidly added at room temperature and under argon atmosphere and the resulting mixture stirred for 24 h. It was then quenched by careful addition of 2N aqueous sodium potassium tartrate, extracted with ether and the combined organic extracts washed with brine, dried and evaporated to give, after purification over silica (eluent, hexane-ethyl acetate, 19:1 (v:v)), 175 mg of pure captioned product (mixture of epimers) as a thick oil.

EXAMPLE 8

Preparation of
[1R-[1β(1R*,5R*)-3aα,4β,7aβ]]-Octahydro-1-[6,6,6-trifluoro-5-hydroxy-1,5-dimethylhexyl]-7a-methyl-1H-inden-4-ol and
[1R-[1β(1R*,5S*)-3aα,4β,7aβ]]Octahydro-1-[6,6,6-trifluoro-5-hydroxy-1,5-dimethylhexyl]-7a-methyl-1H-inden-4-ol A solution of 175 mg (0.39 mmol) of the product of Example 7 (mixture of epimers) in 9 mL of methanol was treated with 2.8 g of AG 50W-X4 cation exchange resin (200–400. mesh, Bio-Rad Laboratory, Richmond, CA) and stirred at room temperature for 12 days. The resin was removed by filtration, washed with methanol and the combined filtrates evaporated to dryness. The residue was purified by rapid filtration through silica (eluent: hexane-ethyl acetate, 9:1 (v:v)), then the two epimers were separated by high performance liquid chromatography, using a Magnum 9 Partisil-10 silica column (Whatman Inc., Clifton, N.J.) and eluting with chloroform/ethyl acetate (5:1 (v:v)) to, give 65 mg of crystalline 5R* product, m.p. 110°–111° C., [α]$^{25}$D+40.3° (c 0.2 in chloroform) retention time 16.4 minutes, the structure of which was confirmed by X-ray crystallographic analysis and 55 mg of 5S* product, [α]$^{25}$D+31.6° (c 0.2 in chloroform), as a thick oil, retention time 15.2 minutes.

EXAMPLE 9

Preparation of
[1R-[1β(1R*,5R*),3aα,4β,7aβ]]-Octahydro-1-6,6,6-trifluoro-5-(trimethylsilyloxy)-1,5-dimethylhexyl]-7a-methyl-1H-inden-4-one A solution of 50 mg (0.15 mmol) of the 5R* diol product of Example 8 in 2 mL of methylene chloride was added to a slurry of 97 mg (0.45 mmol) of pyridinium chlorochromate in 4 mL of methylene chloride and the resulting mixture stirred at room temperature for 1.5 h. It was then diluted with 10 mL of ether, stirred for 15 min, filtered through Celite ® and the residue of the filtration triturated several times with ether and the trituration extracts combined, filtered and evaporated to dryness. The residue was purified by flash chromatography (eluent: hexane-ethyl acetate, 3:1 (v:v)) to give 49 mg of product. This was dissolved in 4 mL of anhydrous methylene chloride, treated with 0.13 mL (0.89 mmol) of trimethylsilylimidazole and stirred at room temperature under argon for 22 h. After addition of 0.5 mL of water, the mixture was stirred for an additional 20 min, then diluted with water and extracted with ethyl acetate. The organic extracts were washed with water and brine, dried (Na$_2$, SO$_4$) and evaporated to dryness. The residue was purified by flash chromatography (eluting with hexane-ethyl acetate, 4:1 (v:v)) to give 51 mg of captioned product as a thick oil.

EXAMPLE 10

Preparation of
[1R-[1β(1R*,5S*),3aα,4β,7aβ]]-Octahydro-1-[6,6,6-trifluoro-5-(trimethylsilyloxy)-1,5-dimethylhexyl]-7a-methyl-1H-inden-4-one Following the procedure described in Example 9, 56 mg of 5S* diol product of Example 8 was converted to 59 mg of the above-captioned product.

EXAMPLE 11

Preparation of
26,26,26-Trifluoro-1α,25R-dihydroxycholecalciferol

A solution of 141 mg (0.23 mmol) of [3S-(3α,5β,Z)]-2-[2-methylene-3,5-bis[[(1,1-dimethylethyl)dimethylsilyl]oxy]cyclohexylidene]ethyldiphenyl phosphine oxide in 6 mL of anhydrous tetrahydrofuran was cooled at −78° C. and treated dropwise and under argon with 0.137 mL (0.22 mmol) of a 1.6 molar solution of n-butyllithium in hexane. After stirring for 5 min, a solution of 51 mg (0.13 mmol) of the ketone product of Example 9 in 1.5 mL of tetrahydrofuran was added dropwise to the deep orange phosphinoxy carbanion solution and the resulting mixture stirred at −78° C. for 1.5 h. It was then treated with 3 mL of a 1:1 (v:v) mixture of 2N potassium sodium tartrate and 2N potassium bicarbonate solution, allowed to come to room temperature, diluted with water and extracted with water and extracted with ethyl acetate. The combined organic layers were washed with brine, dried and evaporated to dryness. The residue was purified by fast filtration through silica eluted with hexane-ethyl acetate, 20:1 (v:v), then dissolved in 0.5 mL of methylene chloride and 5 mL of methanol and stirred at room temperature over-night with 2 g of AG 50W-X4 cation exchange resin (Bio-Rad Laboratories, Richmond, Calif.). After filtration and evaporation of the solvent, the residue was purified by flash chromatography, using hexane-ethyl acetate (1:2) as eluent to give 23 mg of product as a white amorphous powder, $^1$H NMR (400 MHz, CD$_3$OD) 0.60 (s, 3H), 0.99 (d, J=6.4, 3H), 1.30 (s, 3H), 4.15 (m, 1H), 4.38 (m, 1H), d 4.90 (br s, 1H), 5.31 (br s, 1H), 6.10 (dm, J=11.2 Hz, 1H), 6.34 (d, J=11.2 Hz, 1H).

EXAMPLE 12

Preparation of 26,26,26-trifluoro-1α,25S-dihydroxycholecalciferol

Following the procedure of Example 11, 58 mg of the ketone product of Example 10 were converted to 59 mg of 26,26,26-trifluoro-1α,25S-dihydroxycholecalciferol.

$^1$H NMR (400 MHz, CD$_3$OD) 0.58 (s, 3H), 0.97 (d, J=6.8 Hz, 3H), 1.28 (s, 3H), d 4.13 (m, 1H), d 4.36 (m, 1H), 4.90 (br s, 1H), 5.29 (br s, 1H), 6.09 (d, J=11.2 Hz, 1H), 6.32 (d, J=11.2 Hz, 1H).

EXAMPLE 13

| Item | Ingredients | mg/capsule | | |
|---|---|---|---|---|
| 1. | product of the invention | 0.00010 | 0.00025 | 0.00050 |
| 2. | Polyethylene glycol 400 (PEG 400) | 200.00 | 200.00 | 200.00 |
| 3. | butylated hydroxy anisole (BHA) | 0.100 | 0.100 | 0.100 |
| 4. | ascorbyl palmitate | 1.00 | 1.00 | 1.00 |

Procedure:
Dissolve items 1, 3 and 4 in item 2, under a blanket of nitrogen and encapsulate.

EXAMPLE 14

| Item | Ingredients | mg/capsule | | |
|---|---|---|---|---|
| 1. | product of the invention | 0.00010 | 0.00025 | 0.00050 |
| 2. | Polyethylene glycol 400 (PEG 400) | 200.00 | 200.00 | 200.00 |
| 3. | butylated hydroxy anisole (BHA) | 0.100 | 0.100 | 0.100 |
| 4. | ascorbyl palmitate | 1.00 | 1.00 | 1.00 |

Procedure:
Dissolve items 1, 3 and 4 in item 2, under a blanket of nitrogen and encapsulate.

| Item | Ingredients | | |
|---|---|---|---|
| 1. | product of the invention | 0.10 mg | 0.50 mg |
| 2. | 95% ethanol-5% water | 2.00 ml | 3.00 ml |

Procedure
Dissolve item 1 in item 2 under a blanket of nitrogen and inject intramuscularly.

EXAMPLE 15

Subject: Anti-proliferative and differentiation-inducing effects of 26,26,26,-trifluoro-1α,25R-dihydroxycholecalciferol and 26,26,26,-trifluoro-1α,25S-dihydroxycholecalciferol.

General experimental description

Cultures of HL-60 cells were established in the absence (control) or presence of various concentrations of the test compounds. After a 4-day incubation period, the cultures were evaluated for proliferation of tumor cells, tumor cell viability, and cellular differentiation. Proliferation was assessed by directly enumerating the increased number of tumor cells resulting from incubation. Viability was determined by dye exclusion technique to learn whether any of the compounds were lethal to cultured HL-60 cells. Cellular differentiation was evaluated by determining the number of cells which had acquired the enzymes necessary to support a respiratory burst such activity being characteristic of mature macrophages and granulocytes.

Methods

Tissue culture medium used in these experiments was RPMI-1640 supplemented prior to use to 10% v/v with fetal bovine serum (heat inactivated at 56° C. for 30 minutes), to 130 units per ml with penicillin and 130 μg per ml with streptomycin, and to an additional 1.6 millimolar with L-glutamine.

Experimental compounds were dissolved in sufficient ethanol to yield stock solutions of $1 \times 10^{-3}$ molar. Reduced lighting was employed when working with compounds and stock solutions were stored in the dark at −20° C. in an argon atmosphere. Compounds were diluted with tissue culture medium and added to flasks containing HL-60 cells to achieve the final concentrations described in each experiment.

The promyelocytic (HL-60) tumor cell line was derived from a patient with acute promyelocytic leukemia. HL-60 cells were maintained in liquid culture by serial weekly passage in tissue culture medium. In any experiment, three replicate flasks were incubated without compound (control) or in the presence of varying concentrations of compound. After 4 days of incubation at 37° C. in a humidified atmosphere of 5% CO$_2$ in air, cultures were evaluated for tumor cell proliferation, viability and differentiation.

Quantitation of proliferation was done by enumerating the number of HL-60 cells in each individual flask (3 flasks per experimental point) using a model ZBI Coulter Counter. Results are shown as the number of cells per ml of tissue culture medium expressed as the mean±standard deviation and as percent reduction of cell number calculated according to the formula:

$$1 - \left[ \frac{\text{mean number of cells in experimental cultures}}{\text{mean number of cells in control cultures}} \right] \times 100.$$

Experimental cultures with the same or slightly greater cell numbers than control cultures are reported as zero percent reduction.

Viability of tumor cells was determined by the method of trypan blue dye exclusion. Cells in tissue culture medium were added to a four-fold larger volume of 0.4% trypan blue in saline. Cells were scored as viable upon microscopic examination if they excluded dye and as dead if they were stained blue. The viability of cells from all experimental cultures was never less than that from control cultures indicating that the compounds tested were not toxic to HL-60 cells in the concentrations employed.

Quantitation of differentiated cells was done by the biochemical method of nitroblue tetrazolium (NBT) reduction. Sufficient cells were pooled from replicate cultures, centrifuged at 220×g, washed once with serum free tissue culture medium, and resuspended to $1 \times 10^6$ cells per ml in $Ca^{++}$—$Mg^{++}$-deficient phosphate buffered saline (prepared by supplementing $Ca^{++}$—$Mg^{++}$-free phosphate buffered saline (PBS) to 10% v/v with heat-inactivated fetal bovine serum). Nitroblue tetrazolium was dissolved at 1 mg per ml in $Ca^{++}$—$Mg^{++}$-deficient PBS with gentle heating and mixing. Tetradecanoyl phorbol acetate (TPA) was dissolved at 1 mg per ml in ethanol and stored at $-20°$ C. Just prior to use, a working solution of TPA was prepared by diluting the stock concentration 100-fold with $Ca^{++}$—$Mg^{++}$-deficient PBS. The test was done in $12 \times 75$ mm tubes by adding 0.5 ml $Ca^{++}$—$Mg^{++}$-deficient PBS, 1.0 ml of HL-60 cells, 0.5 ml of NBT solution, and 0.02 ml of the working TPA solution. After mixing, the tubes were incubated in a 37° C. water bath for 25 minutes then transferred to ice. Undifferentiated and differentiated cells present in any sample were determined microscopically by surveying 200-400 cells per sample. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results are expressed as the percentage of differentiated cells present in any sample as calculated according to the formula:

$$100 \times \frac{\text{number of formazan positive cells}}{\text{total number of cells counted.}}$$

The results obtained are summarized in Table I.

tive effect. With the experimental methods employed, the maximal anti-proliferative effect was seen at concentrations in excess of $10 \times 10^{-9}$ molar since higher concentrations of 100 and $1000 \times 10^{-9}$ molar were only slightly more effective. Cells from each of the cultures were assessed for differentiation by the method of NBT reduction as also shown in Table I. In contrast to cells from control cultures, a portion of the cells from experimental cultures had synthesized the enzymes necessary to reduce NBT to formazan and were thus judged to be differentiated. Moreover, the proportion of differentiated cells present in any culture was directly related to the concentration of compound present during incubation. Similar to the anti-proliferative effect, the differentiation-inducing effect of the compounds was maximal at approximately $10 \times 10^{-9}$ molar.

Taken together, these data indicate that the products of the invention restrained the proliferation of human promyelocytic tumor cells even though they were not toxic to the cells. Furthermore, cells cultured in low concentrations of the compounds ($1 \times 10^{-9}$ to $10 \times 10^{-9}$ molar) were induced to differentiate toward a more mature cell type as evidenced by the acquisition of enzyme activity. It is expected, then, that each of these compounds is useful as a unique approach to the management of clinical diseases which owe in part to aberrant cellular proliferation and/or differentiation. Exemplary to this issue is the process of neoplastic disease which owes to a perturbation of the normal processes of cellular differentiation.

We claim:

1. 26,26,26-trifluoro-1α,25S-dihydroxycholecalciferol.

2. A pharmaceutical composition suitable for oral administration said composition comprising a therapeutically effective amount of 26,26,26-trifluoro-1α, 25S-dihydroxycholecalciferol and a conventional pharmaceutical carrier material suitable for oral administration.

3. A pharmaceutical composition suitable for paren-

TABLE I

ANTI-PROLIFERATIVE AND DIFFERENTIATION-INDUCING EFFECTS OF
26,26,26-TRIFLUORO-1α,25R-DIHYDROXYCHOLECALCIFEROL AND
26,26,26-TRIFLUORO-1α,25S-DIHYDROXYCHOLECALCIFEROL ON
HL-60 Cells, IN VITRO

| Concentration[a,b] and Compound ($\times 10^{-9}$ molar) | Proliferation[c] | | Differentiation | |
|---|---|---|---|---|
| | HL-60 Cells per ml $\times 10^{-4}$ | % Reduction of cell number | NBT Reduction formazan "+" cells total cells counted | % "+" |
| None (medium control) | 84.7 ± 4.3 | — | 3/368 | <1 |
| Vehicle (0.1% ethanol) | 78.9 ± 4.9 | 0 | 4/356 | 1 |
| 26-(F)$_3$-1α,25R-(OH)$_2$D$_3$ 1 | 59.1 ± 1.9 | 30 | 81/353 | 23 |
| 26-(F)$_3$-1α,25R-(OH)$_2$D$_3$ 10 | 27.2 ± 0.3 | 68 | 299/318 | 94 |
| 26-(F)$_3$-1α,25R-(OH)$_2$D$_3$ 100 | 22.9 ± 1.0 | 73 | 360/367 | 98 |
| 26-(F)$_3$-1α,25R-(OH)$_2$D$_3$ 1000 | 22.0 ± 0.7 | 74 | 340/344 | 99 |
| 26-(F)$_3$-1α,25S-(OH)$_2$D$_3$ 1 | 60.2 ± 3.9 | 29 | 84/334 | 25 |
| 26-(F)$_3$-1α,25S-(OH)$_2$D$_3$ 10 | 27.0 ± 1.4 | 68 | 338/354 | 96 |
| 26-(F)$_3$-1α,25S-(OH)$_2$D$_3$ 100 | 22.3 ± 2.6 | 74 | 323/330 | 98 |
| 26-(F)$_3$-1α,25S-(OH)$_2$D$_3$ 1000 | 20.2 ± 0.5 | 76 | 353/358 | 99 |

[a]Vehicle concentration in all experimental cultures was 0.1% v/v, ethanol.
[b]26-(F)$_3$-1α,25R-(OH)$_2$-D$_3$ is 26,26,26-trifluoro-1,25R-dihydroxycholecalciferol and 26-(F)$_3$-1α,25S-(OH)$_2$-D$_3$ is 26,26,26-trifluoro-1α,25S-dihydroxy-cholecalciferol.
[c]The cell viability in all cultures was greater than 97%. All cultures were initiated with $2 \times 10^4$ HL-60 cells per ml.
Shown for each point is the mean ± S.D.

RESULTS

The experiment described in Table 1 documents that the product of the invention inhibited the proliferation of human promyelocytic tumor cells (HL-60), in vitro in a dose-dependent fashion. The lowest concentration tested ($1 \times 10^{-9}$ molar) was markedly effective and increasing concentrations improved the anti-proliferateral administration said composition comprising a therapeutically effective amount of 26,26,26-trifluoro-1α, 25S-dihydroxycholecalciferol and a conventional pharmaceutical carrier material suitable for parenteral administration.

* * * * *